(12) United States Patent
Kwon et al.

(10) Patent No.: US 12,144,597 B2
(45) Date of Patent: Nov. 19, 2024

(54) APPARATUS AND METHOD FOR DETECTING LIGHT SIGNAL

(71) Applicant: SAMSUNG ELECTRONICS CO., LTD., Suwon-si (KR)

(72) Inventors: Yongjoo Kwon, Yongin-si (KR); Kyoungjun Kim, Yongin-si (KR); Joonhyung Lee, Seongnam-si (KR); Yeolho Lee, Uiwang-si (KR); Seolyoung Choi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 449 days.

(21) Appl. No.: 17/471,862

(22) Filed: Sep. 10, 2021

(65) Prior Publication Data
US 2022/0346657 A1    Nov. 3, 2022

(30) Foreign Application Priority Data

Apr. 29, 2021    (KR) .................. 10-2021-0055951

(51) Int. Cl.
| | |
|---|---|
| *A61B 5/024* | (2006.01) |
| *A61B 5/00* | (2006.01) |
| *A61B 5/026* | (2006.01) |
| *G01J 1/42* | (2006.01) |
| *H05B 47/155* | (2020.01) |

(52) U.S. Cl.
CPC ........ *A61B 5/02427* (2013.01); *A61B 5/0261* (2013.01); *A61B 5/7217* (2013.01); *G01J 1/4204* (2013.01); *H05B 47/155* (2020.01)

(58) Field of Classification Search
CPC .... A61B 2560/0242; A61B 2560/0247; A61B 2562/046; A61B 5/02416; A61B 5/02427; A61B 5/0261; A61B 5/0295; A61B 5/7203; A61B 5/7217; A61B 5/7225
See application file for complete search history.

(56) References Cited

U.S. PATENT DOCUMENTS

| | | | |
|---|---|---|---|
| 9,717,423 B2 | 8/2017 | Loseu et al. | |
| 2014/0213863 A1 | 7/2014 | Loseu et al. | |
| 2014/0275852 A1* | 9/2014 | Hong | ................ A61B 5/0002 600/479 |

(Continued)

FOREIGN PATENT DOCUMENTS

KR    10-1760511 B1    7/2017

OTHER PUBLICATIONS

Communication dated Mar. 29, 2022 issued by the European Patent Office in European Application No. 21203134.8.

*Primary Examiner* — Katherine L Fernandez
(74) *Attorney, Agent, or Firm* — Sughrue Mion, PLLC

(57) ABSTRACT

Provided is an apparatus configured to detect a light signal, the apparatus including a light source configured to radiate light toward an object, a light receiver configured to receive an ambient light and a transmitted light corresponding to the light radiated toward the object from the light source, at least one processor configured to control the light source to be turned off such that a first output signal is generated by the light receiver and control the light source to be turned on such that a second output signal is generated by the light receiver, and an operator configured to generate a transmitted light signal from which noise is removed by differentially operating the second output signal from the first output signal.

17 Claims, 15 Drawing Sheets

(56) References Cited

U.S. PATENT DOCUMENTS

| | | |
|---|---|---|
| 2018/0007296 A1 | 1/2018 | Ayers et al. |
| 2018/0376090 A1* | 12/2018 | Liu ........................ H04N 25/75 |
| 2020/0205680 A1* | 7/2020 | Boukhayma ........... H04N 25/77 |
| 2020/0390344 A1 | 12/2020 | Park et al. |

* cited by examiner

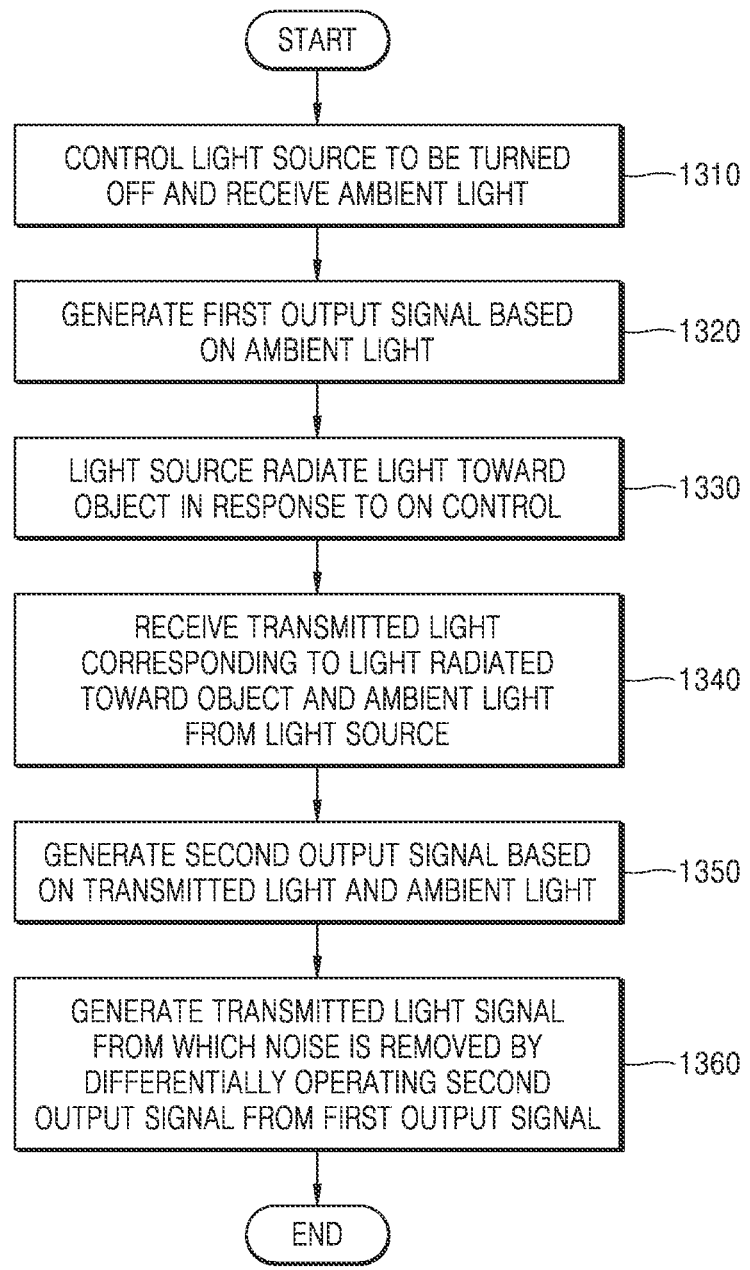

APPARATUS AND METHOD FOR DETECTING LIGHT SIGNAL

CROSS-REFERENCE TO RELATED APPLICATION

This application is based on and claims priority under 35 U.S.C. § 119 to Korean Patent Application No. 10-2021-0055951, filed on Apr. 29, 2021, in the Korean Intellectual Property Office, the disclosure of which is incorporated by reference herein in its entirety.

BACKGROUND

1. Field

Example embodiments of the present disclosure relate to apparatuses and methods for detecting light signals.

2. Description of Related Art

An apparatus for detecting a light signal may radiate light toward an object, receive reflected, transmitted, or scattered light from the object, and then perform an operation on the received light in order to detect a characteristic or property of the object. The light radiated toward the object may be output from a light source. However, according to an environment in which the apparatus for detecting the light signal is used, the apparatus for detecting the light signal may receive not only the light emitted from the light source but also ambient light. Due to noise caused by the ambient light, the apparatus for detecting the light signal may not obtain accurate information about the object. Accordingly, a technology of obtaining accurate information even in an environment in which ambient light is present is required.

SUMMARY

One or more example embodiments provide apparatuses and methods for detecting light signals.

One or more example embodiments also provide computer-readable recording media in which a program for executing the methods on a computer is recorded.

The technical problem to be achieved by example embodiment is not limited to the technical problems as described above, and other technical problems may be inferred from the following embodiments.

Additional aspects will be set forth in part in the description which follows and, in part, will be apparent from the description, or may be learned by practice of example embodiments of the disclosure.

According to an aspect of an example embodiment, there is provided an apparatus configured to detect a light signal, the apparatus including a light source configured to radiate light toward an object, a light receiver configured to receive an ambient light and a transmitted light corresponding to the light radiated toward the object from the light source, at least one processor configured to control the light source to be turned off such that a first output signal is generated by the light receiver and control the light source to be turned on such that a second output signal is generated by the light receiver, and an operator configured to generate a transmitted light signal from which noise is removed by differentially operating the second output signal from the first output signal.

The light receiver may be further configured to generate the first output signal based on the ambient light when the light source is controlled to be turned off, and the first output signal may include ambient light noise generated from the ambient light and reset noise detected in a reset state of the light receiver.

The light receiver may be further configured to generate the second output signal based on the transmitted light and the ambient light when the light source is controlled to be turned on, and the second output signal may include the transmitted light signal generated from the transmitted light, ambient light noise generated from the ambient light, and reset noise detected in a reset state of the light receiver.

The removed noise may include the ambient light noise and the reset noise.

The light receiver may include a photodiode, a reset transistor, and a transfer transistor, the photodiode may be configured to receive the transmitted light and the ambient light, the reset transistor may be configured to reset the light receiver based on a reset signal input through a reset gate, and the transfer transistor may be connected in series with the photodiode, the transfer transistor being configured to transmit a signal generated by the photodiode based on a transfer signal input through a transfer gate.

The at least one processor may be further configured to reset the light receiver by applying the reset signal to the reset transistor before generating the first output signal and the second output signal.

The at least one processor may be further configured to control the light source to be turned off to generate the first output signal and apply the transfer signal to the transfer transistor, and the light receiver may be further configured to receive the ambient light from among the transmitted light and the ambient light based on the transfer signal, and generate the first output signal based on the received ambient light.

The at least one processor may be further configured to control the light source to be turned on to generate the second output signal and apply the transfer signal to the transfer transistor, and the light receiver may be further configured to receive the transmitted light and the ambient light based on the transfer signal, and generate the second output signal based on the received transmitted light and the received ambient light.

The operator may be further configured to reduce a ramp signal when the first output signal is received, and perform down counting from a time when the ramp signal is reduced to a time when a magnitude of the ramp signal is less than or equal to a magnitude of the first output signal.

The operator may be further configured to reduce the ramp signal when the second output signal is received, and perform up counting from the time when the ramp signal is reduced to a time when the magnitude of the ramp signal is less than or equal to a magnitude of the second output signal.

The operator may be further configured to store a result of down counting, differentially operate the second output signal from the first output signal by performing up counting from the stored result of down counting, and generate the transmitted light signal.

The result of down counting may correspond to the first output signal and may include information about the noise, and the result of up counting may correspond to the second output signal and may include information about the noise and information about the transmitted light.

The apparatus may further include a light receiver array comprising a plurality of light receivers arranged along a plurality of rows and a plurality of columns, the plurality of light receivers including the light receiver, the at least one processor may be further configured to individually apply a select signal to each of the plurality of rows of the light receiver array, and light receivers of the plurality of light receivers provided in a row to which the select signal are applied may be configured to generate the first output signal and the second output signal based on the select signal.

The apparatus may further include an operator array that includes a plurality of operators respectively connected to the plurality of columns of the light receiver array, and each of the plurality of operators may be configured to perform a differential operation on the first output signal and the second output signal generated in corresponding columns of the light receiver array.

The operator may include an analog-to-digital converter (ADC) configured to convert the first output signal and the second output signal from an analog signal into a digital signal, and generate the transmitted light signal, which is the digital signal.

The apparatus configured to detect the light signal may be a photoplethysmography (PPG) apparatus, the object may be a user's skin, the light source may be further configured to radiate the light toward a blood vessel inside the user's skin, and the transmitted light signal may include information about a user's pulse wave or blood flow.

According to another aspect of an example embodiment, there is provided a method of detecting a light signal, the method including controlling a light source to be turned off and receiving an ambient light, generating a first output signal based on the ambient light, controlling the light source to be turned on to radiate light toward an object, receiving a transmitted light corresponding to the light radiated toward the object and the ambient light from the light source, generating a second output signal based on the transmitted light and the ambient light, and generating a transmitted light signal from which noise is removed by differentially operating the second output signal from the first output signal.

The method may further include before the controlling of the light source to be turned off and the receiving of the ambient light, resetting the light receiver by applying a reset signal to the light receiver.

The first output signal may include ambient light noise generated from the ambient light and reset noise detected in a reset state of the light receiver, the second output signal may include the transmitted light signal generated from the transmitted light, the ambient light noise and the reset noise, and the removed noise may include the ambient light noise and the reset noise.

The method may further include before the controlling of the light source to be turned off and the receiving of the ambient light, applying a select signal to the light receiver so that a signal generated by the light receiver is output.

Each of the controlling of the light source to be turned off and receiving of the ambient light and the receiving of the transmitted light corresponding to the light radiated toward the object and the ambient light may include applying a transfer signal to the light receiver, and transmitting a signal generated by a photodiode included in the light receiver based on the transfer signal.

The method may further include after the generating of the first output signal, reducing a ramp signal when the first output signal is received by an operator, and performing down counting from a time when the ramp signal is reduced to a time when a magnitude of the ramp signal is less than or equal to a magnitude of the first output signal.

The method may further include after the generating of the second output signal, reducing the ramp signal when the second output signal is received, and performing up counting from the time when the ramp signal is reduced to a time when the magnitude of the ramp signal is less than or equal to a magnitude of the second output signal.

The generating of the transmitted light signal may include storing a result of down counting, differentially operating the second output signal from the first output signal by performing up counting from the stored result of down counting, and generating the transmitted light signal.

The result of down counting may correspond to the first output signal and may include information about the noise, and the result of up counting may correspond to the second output signal and may include information about the noise and information about the transmitted light.

The generating of the transmitted light signal may include converting the first output signal and the second output signal from an analog signal into a digital signal, and generating the transmitted light signal, which is the digital signal, through an operation on the converted signal.

According to yet another aspect of an example embodiment, there is provided a computer-readable recording medium having recorded thereon a program for executing a method on a computer, the method including controlling a light source to be turned off and receiving an ambient light, generating a first output signal based on the ambient light, the light source radiating light toward an object based on an on control, receiving a transmitted light corresponding to the light radiated toward the object and the ambient light from the light source, generating a second output signal based on the transmitted light and the ambient light, and generating a transmitted light signal from which noise is removed by differentially operating the second output signal from the first output signal.

According to yet another aspect of an example embodiment, there is provided an apparatus for detecting a light signal, the apparatus including a light source configured to radiate light toward an object, at least one processor configured to turn the light source on and off, a light receiver configured to receive an ambient light and a transmitted light that is transmitted or reflected from the object that is irradiated with the light from the light source, generate a first output signal based on the light source being turned on, and generate a second output signal based on the light source being turned off, and an operator including at least one processor, the operator being configured to generate a transmitted light signal from which noise is removed by differentially operating the second output signal from the first output signal.

BRIEF DESCRIPTION OF THE DRAWINGS

The above and/or other aspects, features, and advantages of certain example embodiments of the disclosure will be more apparent from the following description taken in conjunction with the accompanying drawings, in which:

FIG. 13 is a flowchart illustrating a method of detecting a light signal according to an example embodiment.

DETAILED DESCRIPTION

Figure 1:
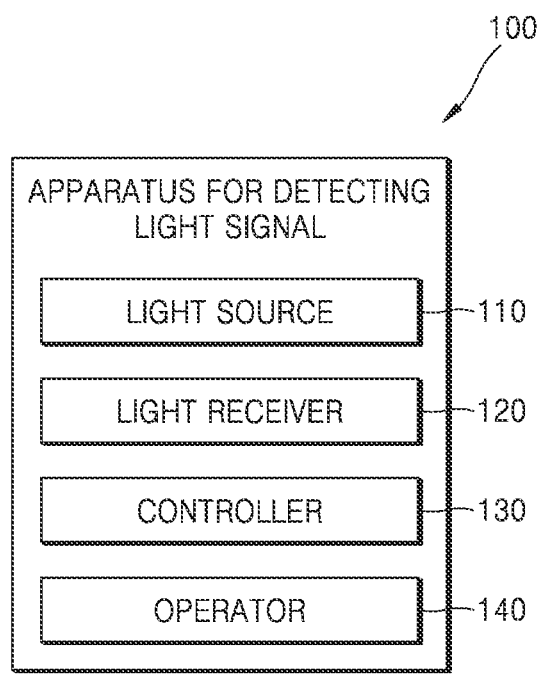
FIG. 1 is a block diagram illustrating a configuration of an apparatus for detecting a light signal according to an example embodiment.

Example embodiments will now be described in detail with reference to the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain aspects.

As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Terminologies used herein are selected as commonly used by those of ordinary skill in the art in consideration of functions of the example embodiment, but may vary according to the technical intention, precedents, or a disclosure of a new technology. Also, in particular cases, some terms are arbitrarily selected by the applicant, and in this case, the meanings of the terms will be described in detail at corresponding parts of the specification. Accordingly, the terms used in the specification should be defined not by simply the names of the terms but based on the meaning and contents of the whole specification.

In the descriptions of the example embodiments, it will be understood that, when an element is referred to as being connected to another element, it may include electrically connected when the element is directly connected to the other element and when the element is indirectly connected to the other element by intervening a constituent element.

It will be further understood that the term "comprises" or "includes" should not be construed as necessarily including various constituent elements and various operations described in the specification, and also should not be construed that portions of the constituent elements or operations of the various constituent elements and various operations may not be included or additional constituent elements and operations may further be included.

It will be understood that, although the terms "first", "second", etc. may be used herein to describe various constituent elements, these constituent elements should not be limited by these terms. The terms are used only for the purpose of distinguishing one component from another component.

The descriptions of the example embodiments should not be interpreted as limiting the scope of right, and embodiments that are readily inferred from the detailed descriptions and example embodiments by those of ordinary skill in the art will be construed as being included in the inventive concept. Reference will now be made in detail to example embodiments of which are illustrated in the accompanying drawings.

FIG. 1 is a block diagram illustrating a configuration of an apparatus 100 for detecting a light signal according to an example embodiment.

Referring to FIG. 1, the apparatus 100 for detecting the light signal may include a light source 110, a light receiver 120, a controller 130, and an operator 140. In the apparatus 100 for detecting the light shown in FIG. 1, only the components related to the example embodiments are illustrated. Accordingly, the apparatus 100 for detecting the light signal may include other general-purpose components other than the components shown in FIG. 1.

The apparatus 100 for detecting the light signal may detect the light signal including information about an object by radiating a light toward the object and receiving a light corresponding to the radiated light. Because characteristics of light reflected from or transmitted through the object also vary according to properties or characteristics of the object, the apparatus 100 for detecting the light signal may obtain the information about the object based on the received light. For example, the apparatus 100 for detecting the light signal may be a photoplethysmography (PPG) apparatus that measures a user's pulse wave or blood flow. According to another example embodiment, the apparatus 100 for detecting the light signal may detect a bio signal such as an electrocardiography (ECG) signal and an electromyography (EMG) signal. This will be described later with reference to FIGS. 3A and 3B.

The light source 110 may radiate light toward the object. The light source 110 may emit the light toward the object by emitting the light in response to an on control (e.g., an control signal to turn on), and may not emit the light toward the object by not emitting the light in response to an off control (e.g., a control signal to turn off). Accordingly, the light source 110 may or may not radiate the light toward the object according to the on/off control. A part of the object to which the light is radiated may vary, and may be determined according to properties and characteristics of the object. For example, the light source 110 may be implemented as a light emitting diode (LED), a laser diode (LD), or a phosphor. However, embodiments are not limited thereto. For example, the light source 110 may include a plurality of light sources, and in this case, each of the plurality of light sources may be designed to emit light of different wavelengths.

The light receiver 120 may receive a transmitted light corresponding to the light radiated toward the object from the light source 110. The transmitted light may include the radiated light reflected from the object, a light scattered inside the object, or a light transmitted through the object.

The light receiver 120 may also receive an ambient light. The ambient light is light independent of the light radiated from the light source 110, and may correspond to a light caused by artificial lighting or direct sunlight around the apparatus 100 for detecting the light signal. The ambient light may be light consistently received by the light receiver 120 irrespective of whether the light source 110 is turned on or off. Accordingly, the light receiver 120 may receive the transmitted light and the ambient light when the light source 110 is turned on, and may receive only the ambient light when the light source 110 is turned off.

For example, the light receiver 120 may be implemented in the form of a charge coupled device (CCD), a complementary image sensor (CIS), or a photoplethysmography sensor. However, this is only an example, and the light receiver 120 is not limited thereto. For example, the light receiver may be implemented as various types of devices receiving and sensing light.

The light receiver 120 may generate the light signal based on the received light. The light receiver 120 may generate a first output signal based on the ambient light when the light source 110 is controlled to be turned off, and generate a second output signal based on the transmitted light and the ambient light when the light source is controlled to be turned on. The second output signal may include information about the transmitted light and noise, whereas the first output signal may include only noise. This will be described later with reference to FIGS. 4A and 4B.

The controller 130 serves to perform overall functions controlling the apparatus 100 for detecting the light signal. For example, the controller 130 may generally control the apparatus 100 for detecting the light signal by executing programs stored in a memory. The controller 130 may control operations of the light source 110, the light receiver 120, the operator 140, and other components included in the apparatus 100 for detecting the light signal.

The controller 130 may control the light source 110 to emit light by turning the light source 110 on, and may control the light source 110 not to emit light by turning the light source 110 off. For example, the controller 130 may control the light source 110 to be turned on by applying an on signal to the light source 110 in an off state. The controller 130 may control the light source 110 to be turned off so that the first output signal is generated from the light receiver 120 and control the light source 110 to be turned on so that the second output signal is generated from the light receiver 120.

The controller 130 may include at least one processor. The processor may be implemented as an array of a plurality of logic gates, or may be implemented as a combination of a general-purpose microprocessor and a memory in which a program executable in the microprocessor is stored. In addition, it may be understood by those skilled in the art to which the example embodiment pertains that the processor may be implemented in other types of hardware.

The operator 140 may receive and process signals generated from the light receiver 120 by receiving the transmitted light or the ambient light. The operator 140 may generate a signal from which noise is removed by performing operations on the received signals. The operator 140 may generate the transmitted light signal by differentially operating the second output signal from the first output signal. Because the second output signal includes only noise and the first output signal includes information about the transmitted light and noise, when the second output signal is differentially operated from the first output signal, only the information about the transmitted light is included and noise may be removed. Accordingly, the transmitted light signal may include only the information about the transmitted light and exclude noise due to the ambient light and other factors. A differential operation method of the operator 140 will be described later with reference to FIG. 8. The operator 140 may include at least one processor.

The apparatus 100 for detecting the light signal may obtain more accurate information about the object by generating the transmitted light signal from which noise is removed through a differential operation.

Figure 2A:
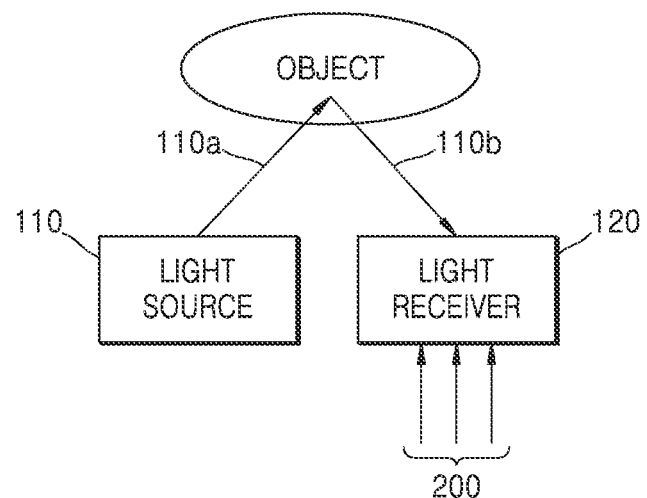
FIGS. 2A and 2B are diagrams illustrating aspects of transmitted light according to example embodiments.
Figure 2B:
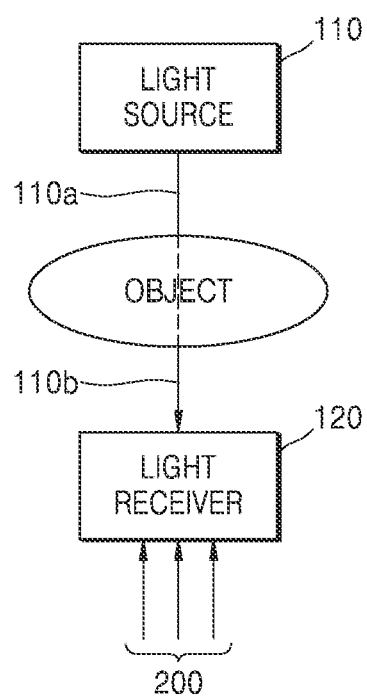

FIGS. 2A and 2B are diagrams illustrating aspects of a transmitted light 110b according to embodiments.

Referring to FIGS. 2A and 2B, the light source 110 may radiate light 110a toward an object, and the light receiver 120 may receive the transmitted light 110b corresponding to the radiated light 110a. Also, the light receiver 120 may receive an ambient light 200. Referring to FIG. 2A, the light 110a radiated toward the object may be reflected from the object and received by the light receiver 120, and referring to FIG. 2B, the light 110a radiated toward the object may transmit through the object and be received by the light receiver 120.

In the example embodiment of FIG. 2A, the radiated light 110a may transmit through a surface of the object, then reflected from the inside of the object, transmit through the surface of the object again, and be received by the light receiver 120. For example, the radiated light 110a may be reflected by another object inside of the object. In another example embodiment, the radiated light 110a may be reflected from the surface of the object and received by the light receiver 120. In this case, the transmitted light 110b corresponding to the radiated light 110a may be a light reflected from the inside or the surface of the object.

In the example embodiment of FIG. 2B, the radiated light 110a may be transmitted through the surface of the object, then pass through the object, be transmitted through an opposite surface of the object again, and be received by the light receiver 120. In this case, the transmitted light 110b corresponding to the radiated light 110a may be a light transmitted through the object.

In another example embodiment, the transmitted light 110b may be a light scattered inside the object.

Aspects of the transmitted light 110b may be variously determined according to characteristics and properties of the object, arrangements of the light source 110 and the light receiver 120, or performance of an apparatus for detecting a light signal.

Figure 3A:
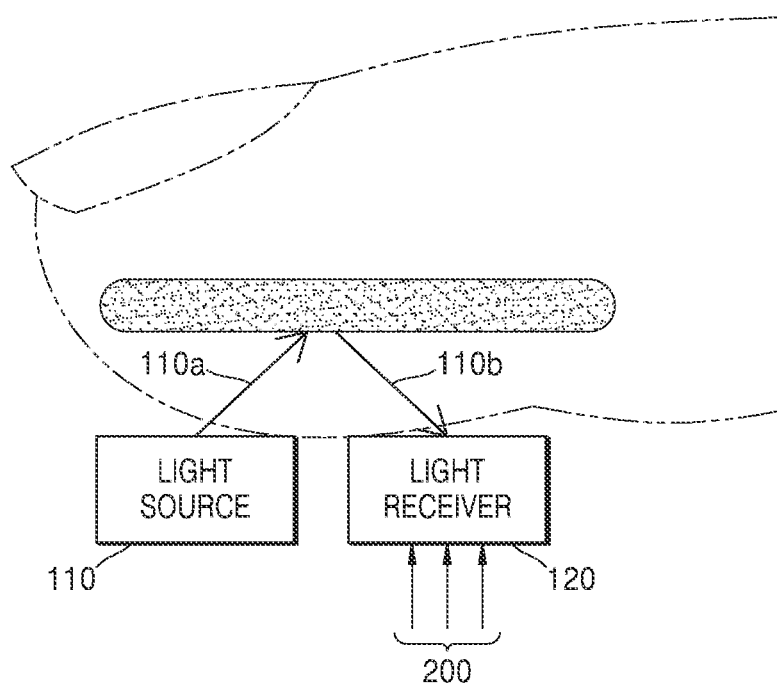
FIGS. 3A and 3B are diagrams illustrating an object according to example embodiments.
Figure 3B:
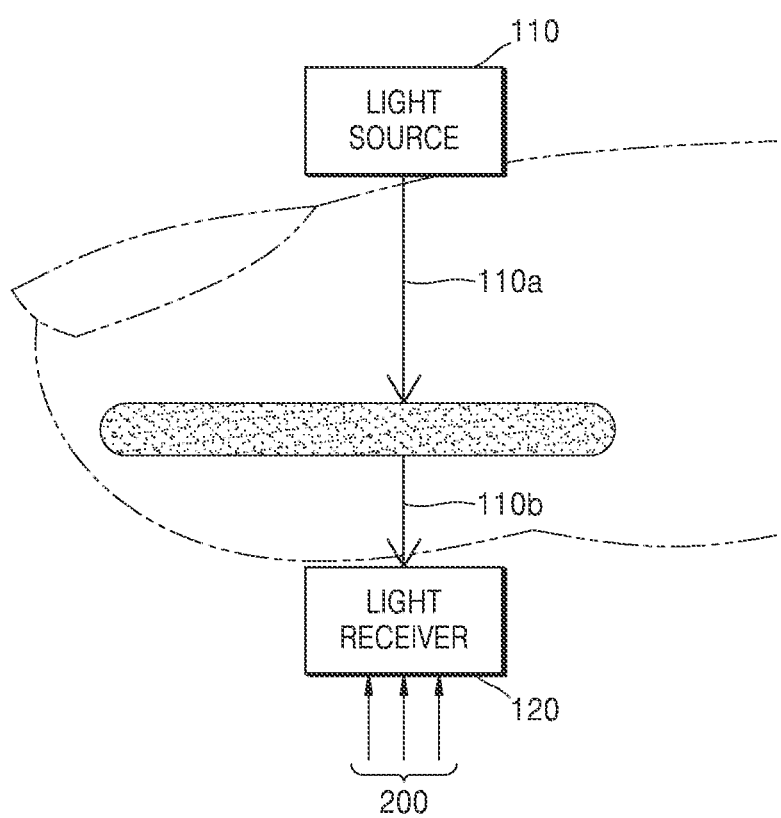

FIGS. 3A and 3B are diagrams illustrating an object according to example embodiments.

Referring to FIGS. 3A and 3B, the light source 110 may radiate the light 110a toward the object, and the light receiver 120 may receive the transmitted light 110b corresponding to the radiated light 110a that is reflected from or transmitted through the object and the ambient light 200.

In the example embodiments of FIGS. 3A and 3B, the object may correspond to a user's skin. The light source 110 may radiate light toward a position of the skin corresponding to a position of a user's blood vessel so that the light reaches the user's blood vessel. For example, the light source 110 may radiate the light toward the position of the skin corresponding to a position through which a user's capillary blood, arterial blood, or venous blood passes.

In this case, an apparatus for detecting a light signal may operate as a photoplethysmography apparatus, and a transmitted light signal may include information about a pulse wave or blood flow obtained from the user's blood vessel.

In the embodiment of FIG. 3A, the radiated light 110a may be transmitted through the skin, then be reflected from the inside of the blood vessel, be transmitted through a surface of the skin again and be received by the light receiver 120. In this case, the transmitted light 110b corresponding to the radiated light 110a may be a light reflected from the inside of the skin which is the object.

In the example embodiment of FIG. 3B, the radiated light 110a may be transmitted through the skin, then pass through the blood vessel, be transmitted through the skin on the opposite side again and be received by the light receiver 120. In this case, the transmitted light 110b corresponding to the radiated light 110a may be a light transmitted through the skin which is the object and the blood vessel inside the object.

In another example embodiment, the transmitted light 110b may be a light scattered inside the user's blood vessel.

Although a user's finger is illustrated in FIGS. 3A and 3B, the object may correspond to skin of various parts through which blood vessels pass, as well as skin of the finger. For example, the skin which is the object may correspond to skin of various parts such as a wrist, an ankle, an arm, and a leg in addition to the user's finger.

Figure 4A:
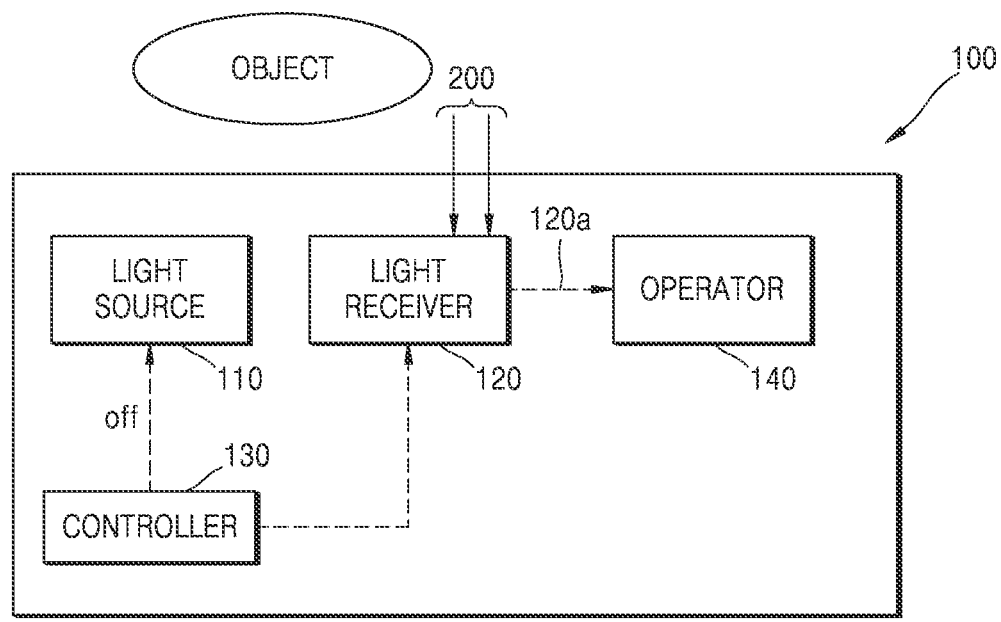
FIG. 4A is a diagram illustrating an operation of an apparatus for detecting a light signal when a light source is controlled to be turned off according to an example embodiment.

FIG. 4A is a diagram illustrating an operation of the apparatus 100 for detecting a light signal when the light source 110 is controlled to be turned off according to an example embodiment.

Referring to FIG. 4A, the controller 130 may control the light source 110 to be turned off and the light receiver 120 may receive only the ambient light 200.

The light receiver 120 may generate a first output signal 120a based on the ambient light 200 based on the light source 110 being controlled to be turned off. Because the light receiver 120 does not receive a transmitted light, the first output signal 120a may exclude information about the transmitted light and include only noise. The first output signal 120a may include ambient light noise which is a signal generated from the ambient light 200 and reset noise detected in a reset state of the light receiver 120. Because a target of detection is the transmitted light rather than the ambient light 200, a signal generated from the ambient light 200 corresponds to noise. A reset of the light receiver 120 will be described later with reference to FIG. 6.

The operator 140 may receive and store the first output signal 120a when the light source 110 is controlled to be turned off.

Figure 4B:
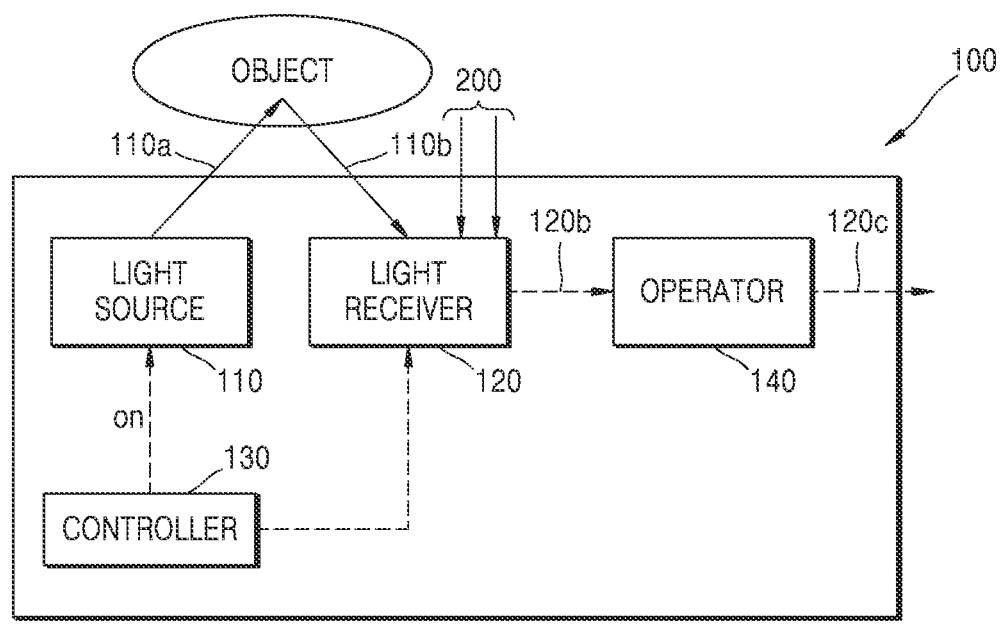
FIG. 4B is a diagram illustrating an operation of an apparatus for detecting a light signal when a light source is controlled to be turned on according to an example embodiment.

FIG. 4B is a diagram illustrating an operation of the apparatus 100 for detecting a light signal when the light source 110 is controlled to be turned on according to an example embodiment.

Referring to FIG. 4B, the controller 130 may control the light source 110 to be turned on and the light receiver 120 may receive the transmitted light 110b and the ambient light 200.

The light receiver 120 may generate a second output signal 120b based on the transmitted light 110b and the ambient light 200 based on the light source 110 being controlled to be turned on. The second output signal 120b may include information about the transmitted light 110b and noise. The second output signal 120b may include a transmitted light signal 120c generated from the transmitted light 110b, ambient light noise that is a signal generated from the ambient light 200, and reset noise detected in a reset state of the light receiver 120.

The operator 140 may receive and store the second output signal 120b when the light source 110 is controlled to be turned on. The operator 140 may receive both a first output signal and the second output signal 120b, and differentially operate the second output signal 120b from the first output signal to generate and output the transmitted light signal 120c from which noise is removed. Here, the noise removed by the operator 140 may correspond to the ambient light noise and the reset noise.

Figure 5:
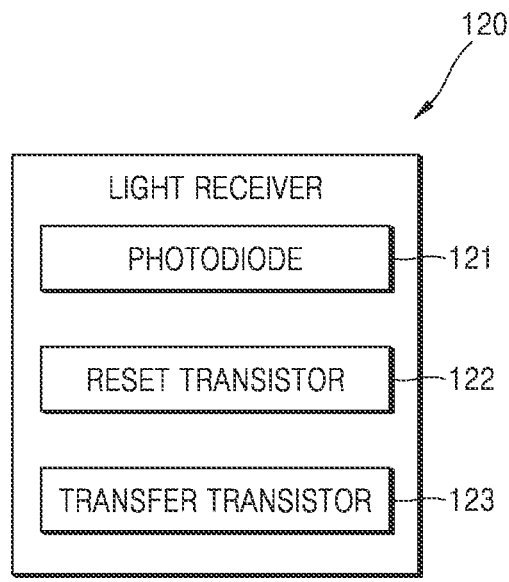
FIG. 5 is a block diagram illustrating a configuration of a light receiver according to an example embodiment.

FIG. 5 is a block diagram illustrating a configuration of the light receiver 120 according to an example embodiment.

Referring to FIG. 5, the light receiver 120 may include a photo diode 121, a reset transistor 122, and a transfer transistor 123. Only the components related to the example embodiments are shown in the light receiver 120 shown in FIG. 5. Accordingly, the light receiver 120 may further include other general-purpose components (e.g., a select transistor and a floating diffusion region) in addition to the components illustrated in FIG. 5.

The photodiode 121 may receive a transmitted light or an ambient light. When the light source 110 is controlled to be turned on, the photodiode 121 may receive the transmitted light and the ambient light, and when the light source 110 is controlled to be turned off, the photodiode 121 may receive only the ambient light. The photodiode 121 may generate a light signal or photoelectrons from the received light.

The reset transistor 122 may reset the light receiver 120 in response to a reset signal received by a controller. The controller may apply the reset signal to the reset transistor 122 through a reset gate so as to reset the light receiver 120. The controller may control the light receiver 120 to reset before generating an output signal. This is to obtain a more accurate signal by reducing noise. However, noise may not be completely removed by reset, and may be partially detected even in the reset state. The reset noise detected in the reset state of the light receiver 120 may be due to, for example, a process error of each component of the light receiver 120, an error in a voltage applied to the light receiver 120, or a time required for propagation of various signals.

The transfer transistor 123 may allow the signal to pass therethrough by opening a path with respect to the signal generated from the photodiode 121 in response to a transfer signal received by the controller. For example, the transfer transistor 123 may transfer the signal generated from the photodiode 121 to the floating diffusion region. Accordingly, when the transfer signal is received, the light receiver 120 may generate the output signal based on the transmitted light or the ambient light. Meanwhile, when the transfer signal is not received, because the transfer transistor 123 does not allow the signal generated from the photodiode 121 to pass therethrough, the signal is not transmitted from the photodiode 121 to other regions, and thus the light receiver 120 does not generate the output signal based on the transmitted light or the ambient light.

Figure 6:
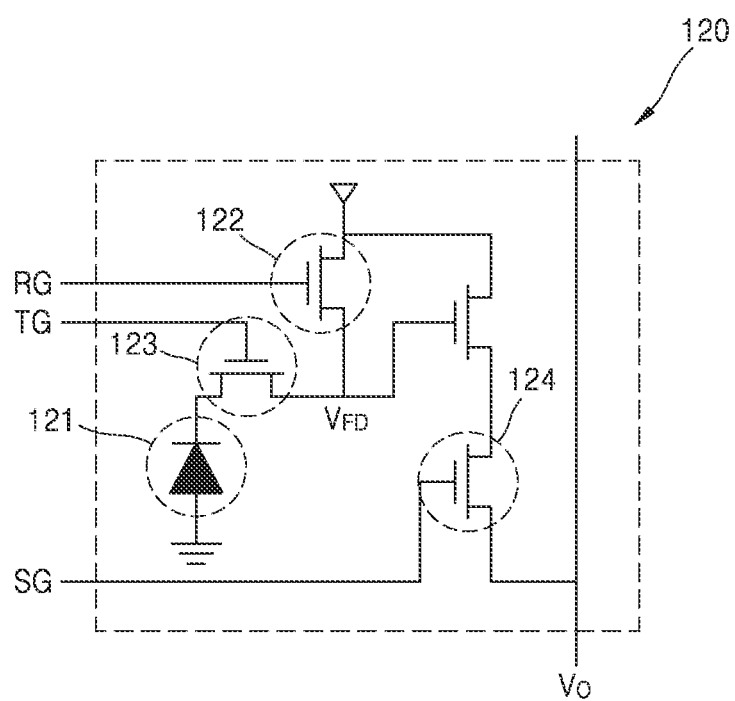
FIG. 6 is a diagram illustrating a circuit diagram of a light receiver according to an example embodiment.

FIG. 6 is a diagram illustrating a circuit diagram of the light receiver 120 according to an example embodiment.

Referring to FIG. 6, the light receiver 120 may include the photodiode 121, the reset transistor 122, the transfer transistor 123, and a select transistor 124. The light receiver 120 may also include a floating diffusion region that is a region through which a floating diffusion voltage $V_{FD}$ flows.

The reset transistor 122 may receive a reset signal through a reset gate by a controller. The reset transistor 122 may reset the light receiver 120 in response to the reset signal. For example, the reset transistor 122 may transmit an initialization voltage to the floating diffusion region in response to the reset signal and discharge free electrons in the light receiver 120. The light receiver 120 may be reset before a first output signal and a second output signal $V_O$ are generated.

The photodiode 121 may be connected in series with the transfer transistor 123 and may transmit a light signal generated from the photodiode 121 to the transfer transistor 123.

The transfer transistor 123 may receive a transfer signal through a transfer gate by the controller. The transfer transistor 123 may operate as a switch and may transmit a light signal in response to the transfer signal. The transfer transistor 123 may transmit the light signal to the floating diffusion region. In this case, the first output signal or the second output signal $V_O$ may be generated from the light receiver 120. The transfer transistor 123 may block transmission of the light signal when the transfer signal is not applied. In this case, the light signal is not transmitted to the floating diffusion region and the first output signal or the second output signal $V_O$ is not generated from the light receiver 120.

Because light is received by the photodiode 121, a reverse bias and a reverse current may occur. Accordingly, as an amount of light (e.g., the number of photons) received by the photodiode 121 increases, a magnitude of the floating diffusion voltage $V_{FD}$ decreases, and a magnitude of the output signal $V_O$ (the first output signal or the second output signal) also decreases. The second output signal generated based on the transmitted light and the ambient light may be smaller than the first output signal generated based on only the ambient light because the second output signal $V_O$ is based on a larger amount of light compared to the first output signal.

The select transistor 124 may receive a select signal through a select gate by the controller. The light receiver 120 may generate and output the output signal $V_O$ (the first output signal or the second output signal) only when the select signal is applied. When the select signal is not applied to the light receiver 120, even if the transmitted light or the ambient light is received by the photodiode 121, the output signal $V_O$ (the first output signal or the second output signal) is not generated. Accordingly, the select signal may be a signal for controlling the light receiver 120 to be turned on.

Figure 7A:
FIGS. 7A, 7B, and 7C are timing diagrams illustrating operations of a controller according to example embodiments.
Figure 7A:
Figure 7B:
Figure 7B:
Figure 7C:
Figure 7C:
Figure 7C:

FIGS. 7A, 7B, and 7C are timing diagrams illustrating operations of a controller according to example embodiments.

Referring to FIGS. 7A, 7B and 7C, horizontal axes of the diagrams represent time axes and vertical axes represent applied signals, and the diagrams represent an on/off signal, a transfer signal $\Phi_T$, and a reset signal $\Phi_R$ with respect to a light source.

In the example embodiment of FIG. 7A, the controller may control the light source and a light receiver to generate a first output signal. The controller may control the light source to be turned off so that the light source does not emit light, and apply the transfer signal $\Phi_T$ to the light receiver so that the light receiver receives an ambient light. The light receiver may receive only the ambient light without receiving a transmitted light, and may generate the first output signal based on the received ambient light.

In the example embodiment of FIG. 7B, the controller may control the light source and the light receiver to generate a second output signal. The controller may control the light source to be turned on so that the light source emits light and apply the transfer signal $\Phi_T$ to the light receiver so that the light receiver receives the transmitted light and the ambient light. The light receiver may receive the transmitted light and the ambient light, and may generate the second output signal based on the received transmitted light and ambient light.

In the example embodiment of FIG. 7C, the controller may control the light source and the light receiver so that the light receiver is reset before the first output signal and the second output signal are generated. The controller may control the light receiver to reset by applying the reset signal $\Phi_R$ to the light receiver before controlling the light source to be turned on and applying the transfer signal $\Phi_T$. The controller may generate the first output signal by applying the transfer signal $\Phi_T$ to the light receiver after applying the reset signal $\Phi_R$. The controller may generate the second output signal by controlling the light source to be turned on and applying the transfer signal $\Phi_T$ to the light receiver again after generating the first output signal. An operator may generate a transmitted light signal by differentially operating the second output signal from the first output signal.

Figure 8:
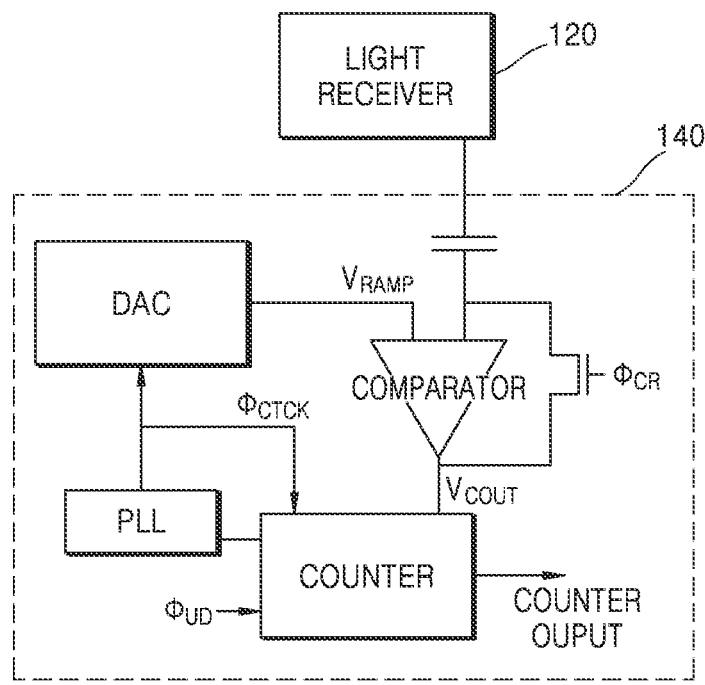
FIG. 8 is a diagram illustrating a circuit diagram of an operator according to an example embodiment.

FIG. 8 is a diagram illustrating a circuit diagram of an operator according to an example embodiment.

Referring to FIG. 8, the operator may include a digital-to-analog converter (DAC), a comparator, a phase-locked loop (PLL), a counter, and a comparator reset transistor. Only the components related to the example embodiments are shown in the operator shown in FIG. 8. Accordingly, the operator may further include other general-purpose components in addition to the components illustrated in FIG. 8.

The DAC includes a current source and may generate a ramp signal $V_{RAMP}$ by receiving a clock signal from the PLL. The DAC may transmit the ramp signal $V_{RAMP}$ to the comparator. The controller may control the comparator to be reset by inputting a comparator reset signal $\Phi_{CR}$ to the comparator reset transistor.

The comparator may perform a comparison operation on an output signal received from a light receiver and the ramp signal $V_{RAMP}$ received from the DAC. The comparator may output a coherent count signal $V_{COUT}$ and, when a magnitude relationship between the output signal and the ramp signal $V_{RAMP}$ changes, output a different count signal $V_{COUT}$. For example, the counter may output the high count signal $V_{COUT}$ when the magnitude of the ramp signal $V_{RAMP}$ is greater than the magnitude of the output signal, and output the low count signal $V_{COUT}$ when the magnitude of the ramp signal $V_{RAMP}$ is smaller than the magnitude of the output signal.

The operator may reduce the ramp signal $V_{RAMP}$ to correspond to the magnitude of the output signal received from the light receiver. The operator may use the comparator to reduce the ramp signal $V_{RAMP}$ until the magnitude of the received output signal is equal to the magnitude of the ramp signal $V_{RAMP}$. As the amount of light received by the light receiver increases, the magnitude of the output signal decreases, and thus a degree of reduction of the ramp signal $V_{RAMP}$ may also increase.

The PLL may apply a counter clock signal $\Phi_{CTCK}$ to the counter while the ramp signal $V_{RAMP}$ decreases. The PLL may apply the counter clock signal $\Phi_{CTCK}$ to the counter until the reduction of the ramp signal $V_{RAMP}$ is completed so that the counter counts the number of clock pulses.

The counter may count clock pulses because the counter clock signal $\Phi_{CTCK}$ is applied. The counter may stop counting when the count signal $V_{COUT}$ received from the comparator changes while counting clock pulses.

The controller may allow the counter to operate in a down count mode or an up count mode by inputting an up-down signal $\Phi_{UD}$ to the counter. For example, the controller may allow the counter to operate in the down count mode by inputting the low up-down signal $\Phi_{UD}$ to the counter, and allow the counter to operate in the up-count mode by inputting the high up-down signal $\Phi_{UD}$ to the counter.

The counter may perform counting on the first output signal and counting on the second output signal in different directions. For example, when down counting is performed on the first output signal, up counting may be performed on the second output signal. The operator may store a down count result with respect to the first output signal, and perform up counting on the second output signal from the stored down count result, thereby differentially operating the second output signal from the first output signal and generating a transmitted light signal.

The operator may include an analogue to digital converter (ADC), and the ADC may include the counter. The ADC may convert the first output signal and the second output signal from an analog signal to a digital signal. When the ADC performs a process of counting clock pulses, the analog signal may be converted into the digital signal. The ADC may generate a transmitted light signal that is the digital signal from the first output signal and the second output signal.

Figure 9:
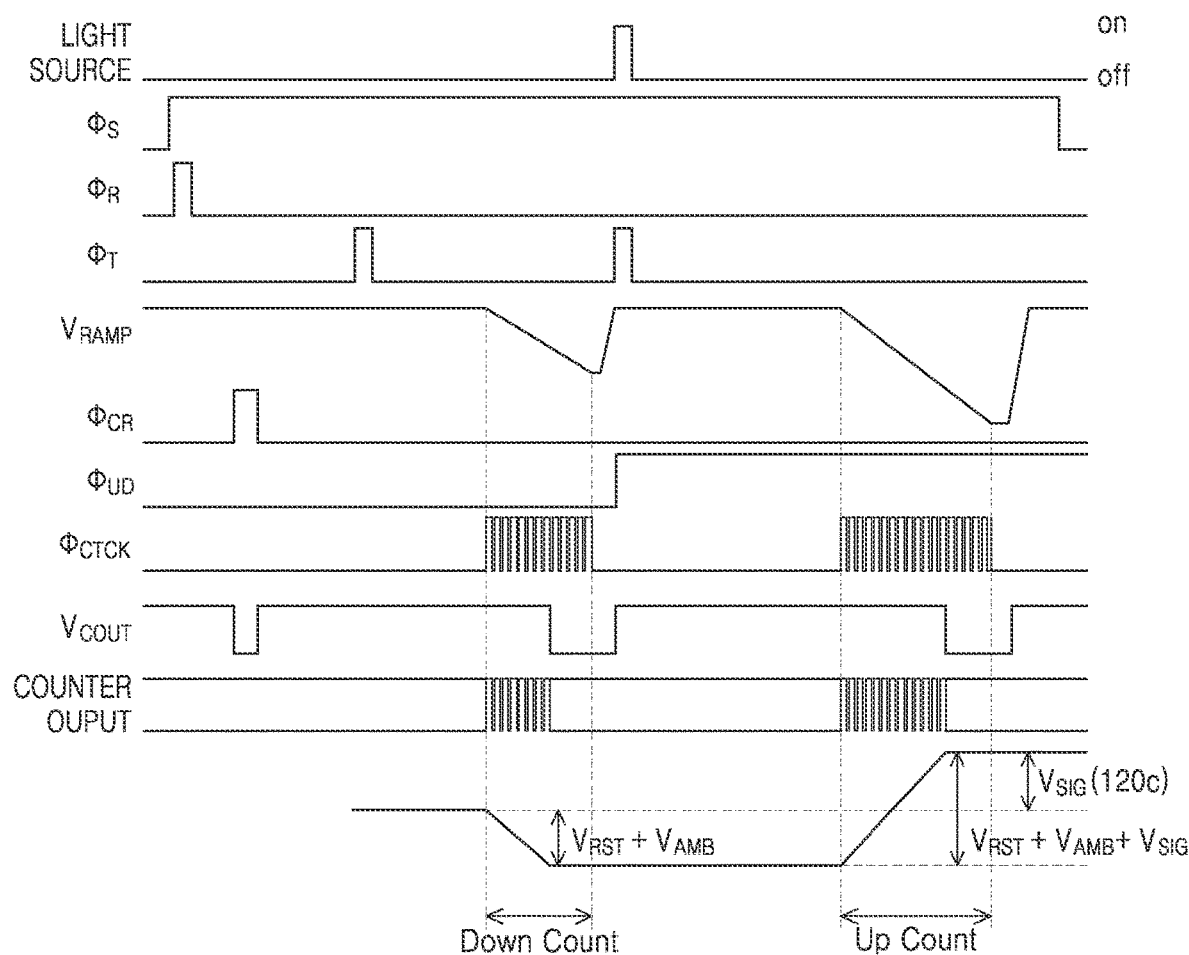
FIG. 9 is a timing diagram illustrating a differential operation method of an operator according to an example embodiment.

FIG. 9 is a timing diagram illustrating a differential operation method of an operator according to an example embodiment.

Referring to FIG. 9, the timing diagram illustrating a process in which the operator differentially operates a second output signal from a first output signal is illustrated.

As described above with reference to FIG. 7C, a controller may perform on/off control of a light source and application of the transfer signal $\Phi_T$ to generate the first output signal and the second output signal after resetting a light receiver. In addition, the controller may apply the select signal $\Phi_S$ to the light receiver to generate and output a signal from the light receiver.

The controller may control a comparator to be reset by inputting a comparator reset signal $\Phi_{CR}$ to the operator before the output signal is transmitted from the light receiver to the operator.

After the comparator is reset, the operator may operate based on a magnitude of the output signal received from the light receiver. When the first output signal is received, the operator may reduce the ramp signal $V_{RAMP}$ to correspond to a magnitude of the received first output signal. The operator may start counting by applying the counter clock signal $\Phi_{CTCK}$ to a counter because a reduction of the ramp signal $V_{RAMP}$ starts. The operator may apply the counter clock signal $\Phi_{CTCK}$ to the counter until the reduction of the ramp signal $V_{RAMP}$ is completed.

When a magnitude of the ramp signal $V_{RAMP}$ is equal to or less than the magnitude of the first output signal, a value of the count signal $V_{COUT}$ may change, and the operator may stop counting in response to the changed count signal $V_{COUT}$. Although the ramp signal $V_{RAMP}$ may be further reduced for a certain time even after the magnitude of the first output signal is smaller than the magnitude of the first output signal, an end of counting does not follow the change in the magnitude of the ramp signal $V_{RAMP}$ but follows the count signal $V_{COUT}$. Therefore, counting may be performed only as much as the magnitude of the first output signal. That is, the operator may perform counting from a time when the ramp signal $V_{RAMP}$ is reduced to a time when the magnitude of the ramp signal $V_{RAMP}$ is equal to or less than the magnitude of the first output signal.

Because the low up-down signal $\Phi_{UD}$ is applied to the operator while counting on the first output signal is performed, the operator may perform down counting on the first output signal. The operator may store a result of down counting. Accordingly, the result of down counting may correspond to the first output signal and may include information about an ambient light noise $V_{AMB}$ and a reset noise $V_{RST}$.

The controller may input the high up-down signal $\Phi_{UD}$ to the operator after down counting on the first output signal ends. Because the second output signal is received, the operator may reduce the ramp signal $V_{RAMP}$ to correspond to the magnitude of the received second output signal. The operator may start counting by applying the counter clock signal $\Phi_{CTCK}$ to the counter because the reduction of the ramp signal $V_{RAMP}$ starts. The operator may apply the counter clock signal $\Phi_{CTCK}$ to the counter until the reduction of the ramp signal $V_{RAMP}$ is completed.

When the magnitude of the ramp signal $V_{RAMP}$ is equal to or less than the magnitude of the second output signal, the value of the count signal $V_{COUT}$ may change, and the operator may stop counting in response to the changed count signal $V_{COUT}$. That is, the operator may perform counting from a time when the ramp signal $V_{RAMP}$ is reduced to a time when the magnitude of the ramp signal $V_{RAMP}$ is equal to or less than the magnitude of the second output signal.

Because the high up-down signal $\Phi_{UD}$ is applied to the operator while counting on the second output signal is performed, the operator may perform up counting on the second output signal. A result of up counting may correspond to the second output signal. The operator may differentially operate the result of up counting from the result of down counting by performing up counting from the stored result of down counting. For example, the operator may differentially operate the second output signal from the first output signal by operating a result of counting corresponding to the output signal.

The result of up counting may correspond to the second output signal and may include information about the transmitted light signal $V_{SIG}$, the ambient light noise $V_{AMB}$, and the reset noise $V_{RST}$. Accordingly, because up counting is performed from the result of down counting, noise may be removed, and only the information about the transmitted light signal $V_{SIG}$ may remain. As described above, the operator may differentially operate the second output signal from the first output signal, thereby removing noise and generating the transmitted light signal 120c including only information about a transmitted light.

Figure 10:
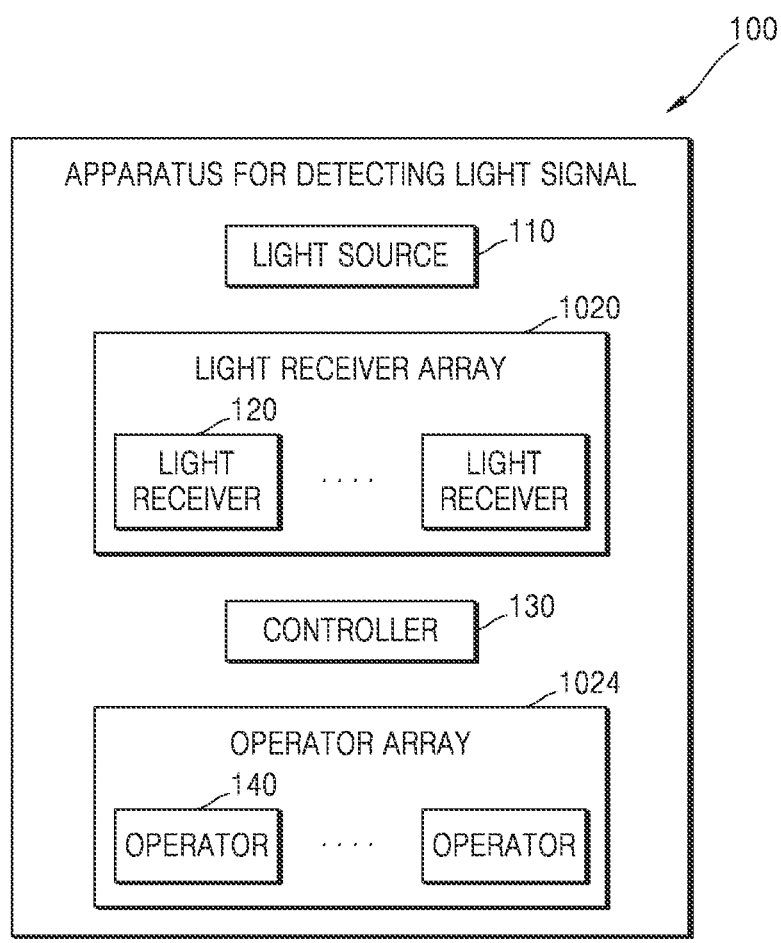
FIG. 10 is a block diagram illustrating a configuration of an apparatus for detecting a light signal according to another example embodiment.

FIG. 10 is a block diagram illustrating a configuration of the 100 apparatus for detecting a light signal according to another example embodiment.

Referring to FIG. 10, the apparatus 100 for detecting the light signal may include the light source 110, a light receiver array 1020, the controller 130, and an operator array 1040. The light receiver array 1020 may include a plurality of light receivers, and the operator array 1040 may include a plurality of operators. In the apparatus 100 for detecting the light signal shown in FIG. 10, only the components related to the example embodiments are illustrated. Accordingly, the apparatus 100 for detecting the light signal may include other general-purpose components other than the components shown in FIG. 10. The light source 110, the light receiver 120, the controller 130, and the operator 140 of FIG. 10 may respectively correspond to the light source 110, the light receiver 120, the controller 130, and the operator 140 of FIG. 1.

Although the apparatus 100 for detecting the light signal includes the single light source 110 in FIG. 10, this is for convenience of description and one or a plurality of light sources 110 may be included. According to another example embodiment, the plurality of light sources 110 may be included in the apparatus 100 for detecting the light signal in the form of an array arranged along a plurality of rows and a plurality of columns. Such a light source array may be disposed separately from the light receiver array 1020, or may be disposed such that each light source of the light source array and each light receiver of the light receiver array 1020 are paired. When the apparatus 100 for detecting the light signal includes a plurality of light sources, the number of light sources radiating light in response to an on control may be variously determined according to a setting. For example, only one light source may radiate light or a plurality of light sources may radiate light in response to the on control. Each of the plurality of light sources may be designed to emit light of different wavelengths.

The light receiver array 1020 may include a plurality of light receivers arranged along a plurality of rows and a plurality of columns. The controller 130 may individually apply a select signal to each row of the light receiver array 1020. For example, the controller 130 may apply the select signal to the light receivers arranged in each row. The light receivers disposed in the row to which the select signal is applied may generate a first output signal and a second output signal in response to the select signal.

The operator array 1040 may include a plurality of operators. Each operator 140 may be connected to each column of the light receiver array 1020. The output signal generated in each column of the light receiver array 1020 may be transmitted to the operator 140 connected to each column. The operator 140 may perform an operation on the output signal generated in the corresponding column of the light receiver array 1020.

Figure 11:
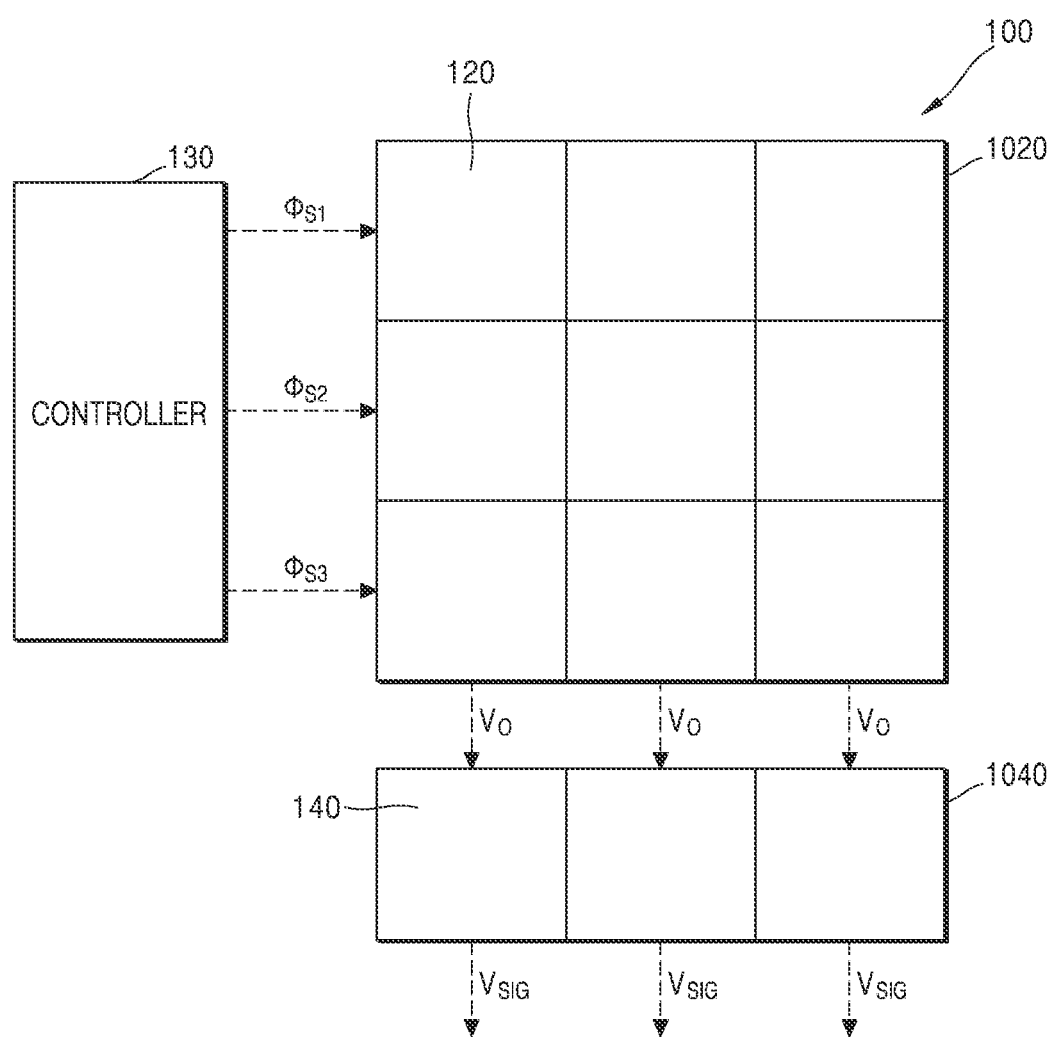
FIG. 11 is a diagram illustrating a structure of the apparatus for detecting the light signal according to the example embodiment of FIG. 10.

FIG. 11 is a diagram illustrating a structure of the apparatus 100 for detecting a light signal according to the example embodiment of FIG. 10.

Referring to FIG. 11, the light receiver array 1020 may include a plurality of light receivers arranged along a plurality of rows and a plurality of columns, and the operator array 1040 may include a plurality of operators respectively connected to the columns of the light receiver array 1020.

The controller 130 may individually apply a select signal to each row of the light receiver array 1020. For example, when the controller 130 applies a select signal $\Phi_{S1}$ to one row of the light receiver array 1020, the output signal $V_O$ may be generated only in a first row of the light receiver array 1020. In this case, each of the operators included in the operator array 1040 may receive the output signal $V_O$ generated by the light receiver 120 disposed in the first row of the connected column, and generate the transmitted light signal $V_{SIG}$ based on the received output signal $V_O$.

Figure 12A:
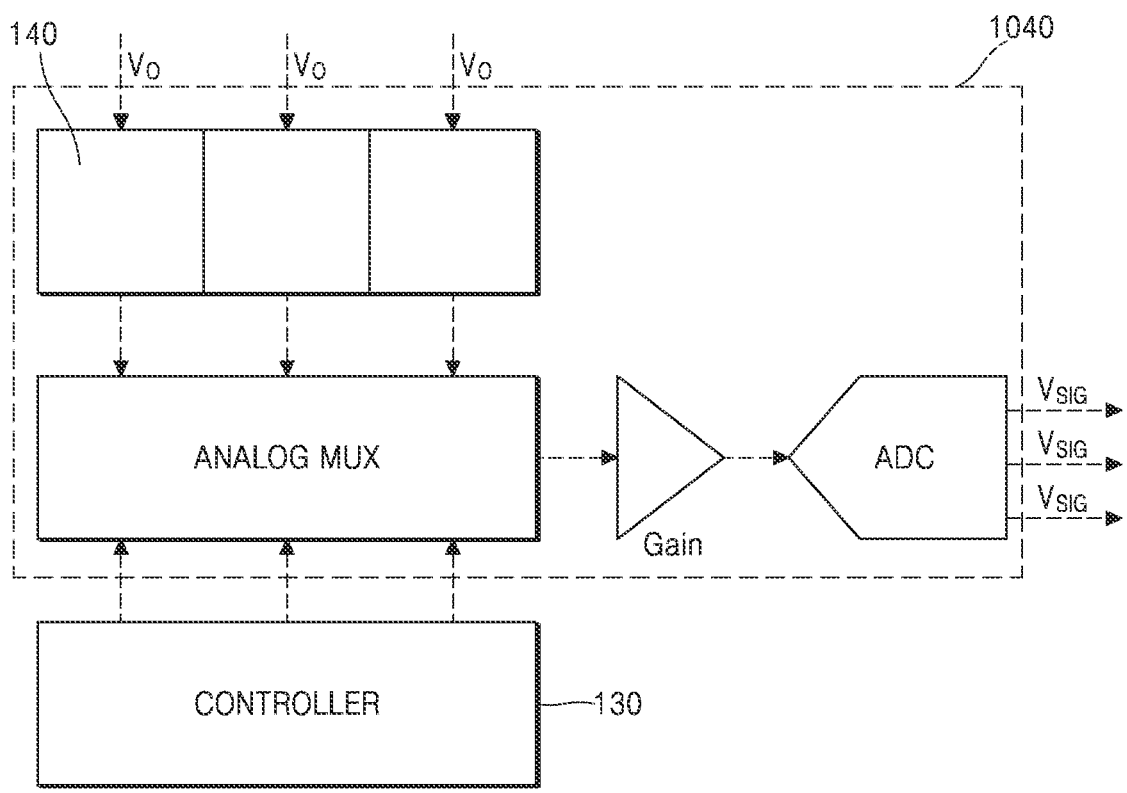
FIGS. 12A, 12B, and 12C are diagrams illustrating structures of an operator array according to example embodiments.
Figure 12B:
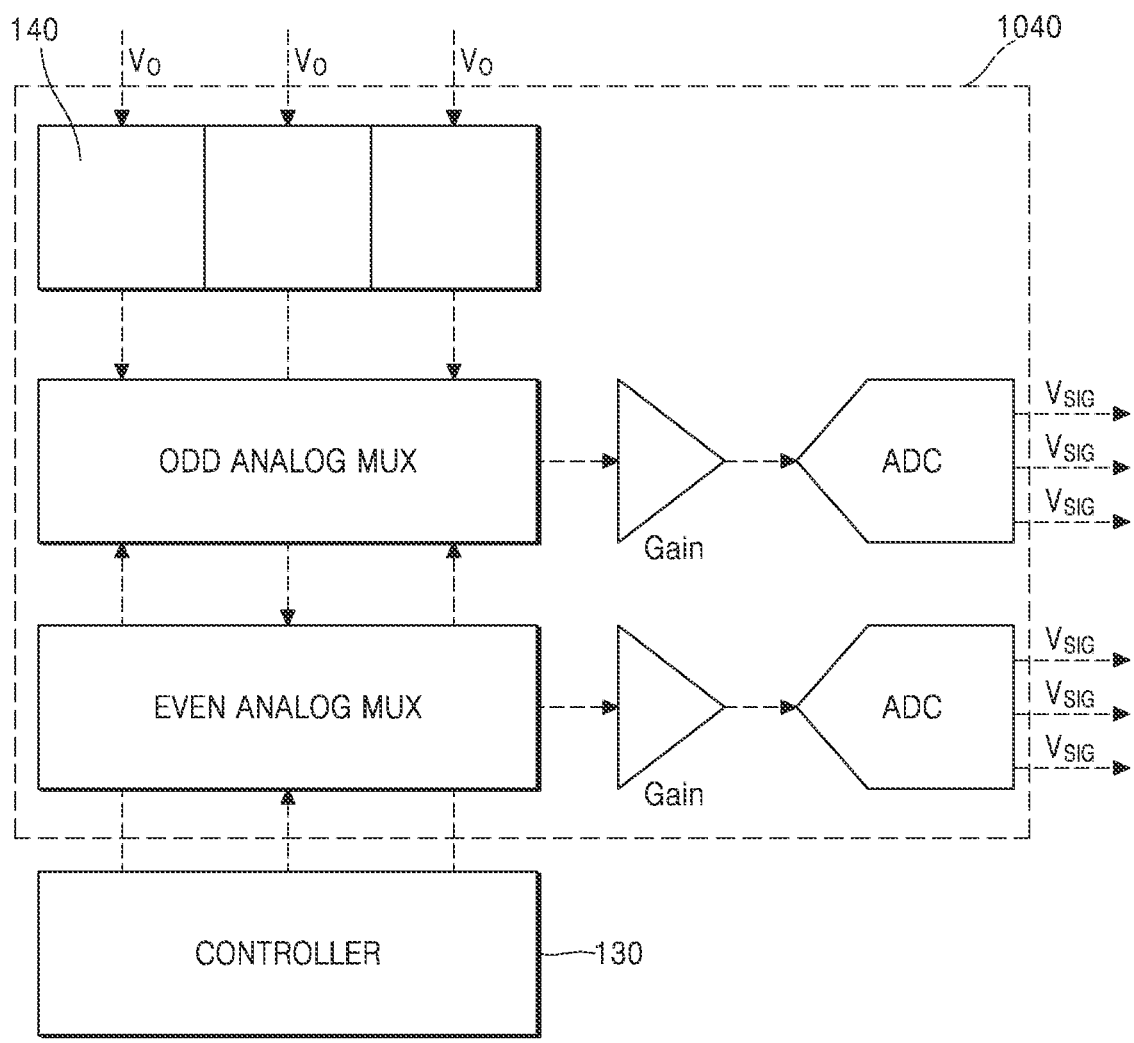
Figure 12C:
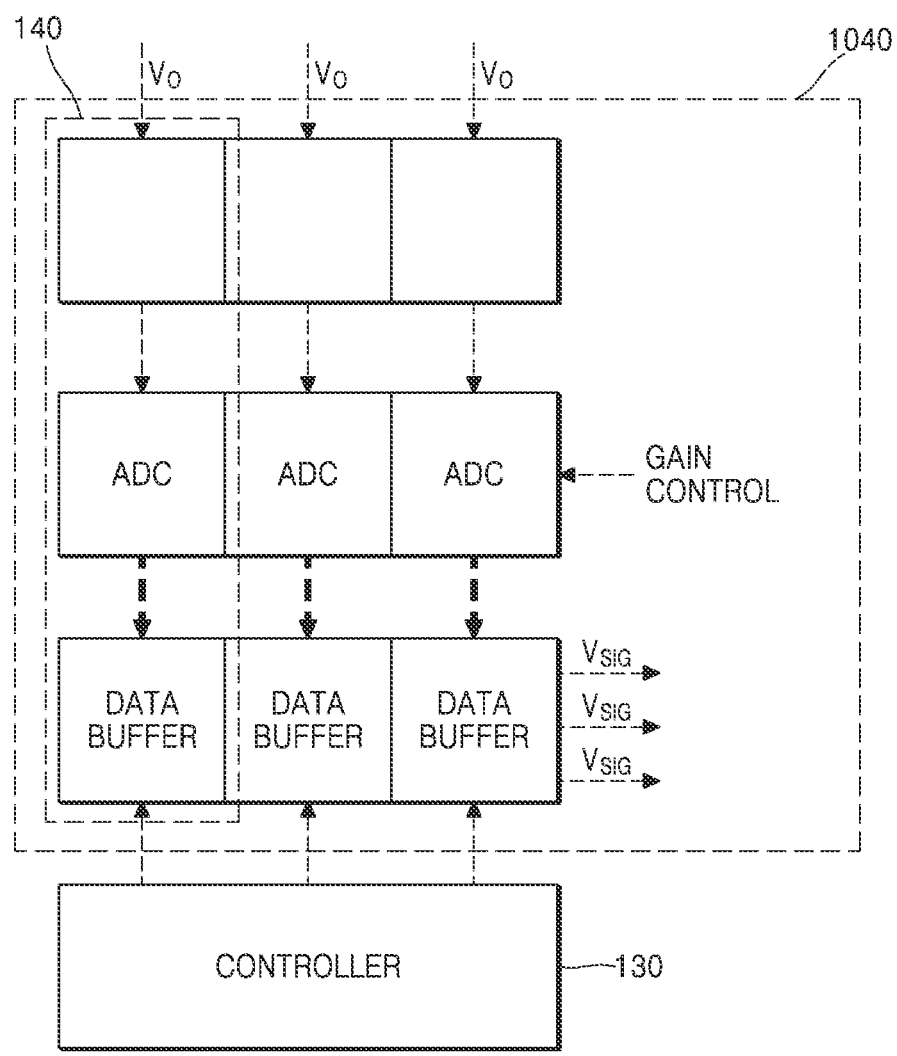

FIGS. 12A, 12B, and 12C are diagrams illustrating structures of the operator array 1040 according to example embodiments.

Referring to FIGS. 12A, 12B, and 12C, the controller 130 may apply a column scanning signal for controlling each column of the operator array 1040 connected to each column of a light receiver to the operator 140.

In the example embodiment of FIG. 12A, the operator array 1040 may include a plurality of operators each connected to each column of the light receiver, an analog multiplexer connected to the operators, an amplifier connected to the analog multiplexer, and an ADC connected to the amplifier. The ADC may generate the transmitted light signal $V_{SIG}$ based on the signal received by each operator 140. During a process of generating the transmitted light signal $V_{SIG}$, counting may be performed by the ADC, and a process before counting may be performed by components in the operator array 1040 other than the ADC.

In the example embodiment of FIG. 12B, the operator array 1040 may include a plurality of operators each connected to each column of the light receiver, an odd analog multiplexer and an even analog multiplexer connected to the operators, an amplifier connected to each multiplexer, and an ADC connected to each amplifier. ADCs may generate the transmitted light signal $V_{SIG}$ based on the signal received by each operator 140. During a process of generating the transmitted light signal $V_{SIG}$, counting may be performed by the ADCs, and a process before counting may be performed by components in the operator array 1040 other than the ADC.

In the example embodiment of FIG. 12C, the operator array 1040 may include a plurality of operators each connected to each column of the light receiver. The operator 140 may include a region including a DAC and a comparator, an ADC connected to the corresponding region, and a data buffer connected to the ADC. In the ADC, a signal is amplified, and the amplified signal may be input to the data buffer. The transmitted light signal $V_{SIG}$ may be output from the data buffer.

FIG. 13 is a flowchart illustrating a method of detecting a light signal according to an example embodiment.

Referring to FIG. 13, the method of detecting the light signal includes operations time serially processed by the apparatus 100 for detecting the light signal illustrated in FIG. 1. Accordingly, the description of the apparatus 100 for detecting the light signal given with reference to FIG. 1 is also applied to the method of FIG. 13 even if omitted below.

In operation 1310, the apparatus for detecting the light signal may control a light source to be turned off and receive an ambient light.

Before operation 1310, the apparatus for detecting the light signal may reset the light receiver by applying a reset signal to the light receiver.

Before operation 1310, the apparatus for detecting the light signal may apply a select signal to the light receiver so that a signal generated by the light receiver may be output.

The apparatus for detecting the light signal may apply a transfer signal to the light receiver. The apparatus for detecting the light signal may allow a signal generated by a photodiode included in the light receiver to pass through in response to the transfer signal.

A first output signal may include ambient light noise generated from the ambient light and reset noise detected in a reset state of the light receiver, a second output signal may include a transmitted light signal generated from a transmitted light, the ambient light noise, and the reset noise, and removed noise may include the ambient light noise and the reset noise.

In operation 1320, the apparatus for detecting the light signal may generate the first output signal based on the received ambient light.

After operation 1320, the apparatus for detecting the light signal may reduce a ramp signal because the first output signal is received by an operator, and perform down counting from a time when the ramp signal is reduced until a time when a magnitude of the ramp signal is less than or equal to a magnitude of the first output signal.

In operation 1330, the light source may radiate light toward an object in response to an on control.

In operation 1340, the apparatus for detecting the light signal may receive the transmitted light and the ambient light corresponding to the light radiated toward the object from the light source.

The apparatus for detecting a light signal may apply a transfer signal to the light receiver. The apparatus for detecting the light signal may allow the signal generated by the photodiode included in the light receiver to pass through in response to the transfer signal.

In operation 1350, the apparatus for detecting the light signal may generate the second output signal based on the transmitted light and the ambient light.

After operation 1350, the apparatus for detecting the light signal may reduce the ramp signal because the second output signal is received by the operator, and perform up counting from the time when the ramp signal is reduced until a time when the magnitude of the ramp signal is less than or equal to a magnitude of the second output signal.

In operation 1360, the apparatus for detecting the light signal may generate a transmitted light signal which noise is removed by differentially operating the second output signal from the first output signal.

The apparatus for detecting the light signal may store a result of down counting and perform up counting from the stored result of down counting to differentially operate the second output signal from the first output signal and generate the transmitted light signal.

The result of down counting may correspond to the first output signal and include information about noise, and the result of up counting may correspond to the second output signal and may include the information about noise and information about the transmitted light.

The apparatus for detecting the light signal may convert the first output signal and the second output signal from an analog signal to a digital signal. The apparatus for detecting the light signal may generate the transmitted light signal which is the digital signal, through an operation on the converted signals.

The operating method of FIG. 13 described above may be recorded in a computer-readable recording medium in which one or more programs including instructions for executing the method are recorded. Examples of non-transitory computer-readable recording media include magnetic media, such as hard disks, floppy disks, and magnetic tape, optical media, such as CD-ROMs and DVDs, magneto-optical media, such as floptical disks, and hardware devices specifically configured to store and execute program instructions, such as read-only memory (ROM), random access memory (RAM), flash memory, etc. Examples of program instructions include machine code produced by a compiler as well as high-level language code that may be executed by a computer by using an interpreter etc.

It should be understood that example embodiments described herein should be considered in a descriptive sense only and not for purposes of limitation. Descriptions of features or aspects within each example embodiment should typically be considered as available for other similar features or aspects in other embodiments. While example embodiments have been described with reference to the figures, it will be understood by those of ordinary skill in the art that various changes in form and details may be made therein without departing from the spirit and scope as defined by the following claims and their equivalents.

What is claimed is:

1. An apparatus configured to detect a light signal, the apparatus comprising:
    a light source configured to radiate light toward an object;
    a light receiver configured to receive an ambient light and a transmitted light corresponding to the light radiated toward the object from the light source;
    at least one processor configured to control the light source to be turned off such that a first output signal is generated by the light receiver and control the light source to be turned on such that a second output signal is generated by the light receiver; and
    an operator configured to generate a transmitted light signal from which noise is removed by differentially operating the second output signal from the first output signal,
    wherein the operator is further configured to:
        reduce a ramp signal when the first output signal is received by the operator;
        perform a first counting from a time when the ramp signal is reduced to a time when a magnitude of the ramp signal is less than or equal to a magnitude of the first output signal; and
        reduce the ramp signal when the second output signal is received,
    wherein differentially operating the second output signal is performing a second counting from the time when the ramp signal is reduced to a time when the magnitude of the ramp signal is less than or equal to a magnitude of the second output signal,
    wherein the second counting starts from a stored result of the first counting, and
    wherein the first counting and the second counting are in different directions.

2. The apparatus of claim 1, wherein the light receiver is further configured to generate the first output signal based on the ambient light when the light source is controlled to be turned off, and
    wherein the first output signal comprises ambient light noise generated from the ambient light and reset noise detected in a reset state of the light receiver.

3. The apparatus of claim 1, wherein the light receiver is further configured to generate the second output signal based on the transmitted light and the ambient light when the light source is controlled to be turned on, and
    wherein the second output signal comprises the transmitted light signal generated from the transmitted light, ambient light noise generated from the ambient light, and reset noise detected in a reset state of the light receiver.

4. The apparatus of claim 3, wherein the removed noise comprises the ambient light noise and the reset noise.

5. The apparatus of claim 1, wherein the light receiver comprises:
    a photodiode configured to receive the transmitted light and the ambient light;
    a reset transistor configured to reset the light receiver based on a reset signal input through a reset gate; and
    a transfer transistor connected in series with the photodiode, the transfer transistor being configured to transmit a signal generated by the photodiode based on a transfer signal input through a transfer gate.

6. The apparatus of claim 5, wherein the at least one processor is further configured to control the light receiver to be reset by applying the reset signal to the reset transistor before generating the first output signal and the second output signal.

7. The apparatus of claim 5, wherein the at least one processor is further configured to control the light source to be turned off to generate the first output signal and apply the transfer signal to the transfer transistor, and
    wherein the light receiver is further configured to receive the ambient light from among the transmitted light and the ambient light based on the transfer signal, and generate the first output signal based on the received ambient light.

8. The apparatus of claim 5, wherein the at least one processor is further configured to control the light source to be turned on to generate the second output signal and apply the transfer signal to the transfer transistor, and
wherein the light receiver is further configured to receive the transmitted light and the ambient light based on the transfer signal, and generate the second output signal based on the received transmitted light and the received ambient light.

9. The apparatus of claim 1, further comprising a light receiver array comprising a plurality of light receivers arranged along a plurality of rows and a plurality of columns, the plurality of light receivers including the light receiver,
wherein the at least one processor is further configured to individually apply a select signal to each of the plurality of rows of the light receiver array, and
wherein light receivers of the plurality of light receivers arranged in a row to which the select signal is applied are configured to generate the first output signal and the second output signal based on the select signal.

10. The apparatus of claim 9, further comprising an operator array comprising a plurality of operators respectively connected to the plurality of columns of the light receiver array, the plurality of operators including the operator, and
wherein each operator of the plurality of operators is configured to perform a differential operation on the first output signal and the second output signal generated in corresponding columns of the light receiver array.

11. The apparatus of claim 1, wherein the operator comprises an analog-to-digital converter (ADC) configured to convert the first output signal and the second output signal from an analog signal into a digital signal, and generate the transmitted light signal, which is the digital signal.

12. The apparatus of claim 1, wherein the apparatus configured to detect the light signal is a photoplethysmography (PPG) apparatus,
wherein the object is a skin of a user,
wherein the light source is further configured to radiate the light toward a blood vessel inside the skin of the user, and
wherein the transmitted light signal comprises information about a pulse wave or blood flow of the user.

13. A method of detecting a light signal, the method comprising:
controlling, by a processor, a light source to be turned off and receiving an ambient light;
generating, by the processor, a first output signal based on the ambient light;
controlling, by the processor, the light source to be turned on to radiate light toward an object;
receiving, by light receiver, a transmitted light corresponding to the light radiated toward the object and the ambient light from the light source;
generating, by the processor, a second output signal based on the transmitted light and the ambient light; and
generating, by an operator, a transmitted light signal from which noise is removed by differentially operating the second output signal from the first output signal;
after the generating the first output signal, reducing, by the operator, a ramp signal when the first output signal is received by the operator;
performing, by the operator, a first counting from a time when the ramp signal is reduced to a time when a magnitude of the ramp signal is less than or equal to a magnitude of the first output signal; and
reducing, by the operator, the ramp signal when the second output signal is received,
wherein differentially operating the second output signal is performing a second counting from the time when the ramp signal is reduced to a time when the magnitude of the ramp signal is less than or equal to a magnitude of the second output signal,
wherein the second counting starts from a stored result of the first counting, and
wherein the first counting and the second counting are in different directions.

14. The method of claim 13, further comprising:
before the controlling the light source to be turned off and the receiving the ambient light, resetting the light receiver by applying a reset signal to the light receiver.

15. The method of claim 13, further comprising:
before the controlling the light source to be turned off and the receiving the ambient light, applying a select signal to the light receiver so that a signal generated by the light receiver is output.

16. The method of claim 13,
wherein each of the controlling the light source to be turned off and the receiving the ambient light and the receiving the transmitted light corresponding to the light radiated toward the object and the ambient light comprises:
applying a transfer signal to the light receiver; and
transmitting a signal generated by a photodiode included in the light receiver based on the transfer signal.

17. The method of claim 13, wherein the generating the transmitted light signal comprises:
converting the first output signal and the second output signal from an analog signal into a digital signal; and
generating the transmitted light signal, which is the digital signal, through an operation on the converted signal.

* * * * *